United States Patent [19]

Holzner

[11] Patent Number: 4,534,509

[45] Date of Patent: Aug. 13, 1985

[54] MULTIPLE COMPARTMENT PLASTIC PACKING

[75] Inventor: Günter Holzner, Carouge, Switzerland

[73] Assignee: Firmenich SA, Switzerland

[21] Appl. No.: 515,515

[22] Filed: Jul. 20, 1983

Related U.S. Application Data

[63] Continuation-in-part of Ser. No. 432,917, Sep. 28, 1982.

[51] Int. Cl.³ .............................................. B65D 81/32
[52] U.S. Cl. ..................................................... 239/34
[58] Field of Search ........................ 239/34, 53, 54, 55, 239/56, 58, 59; 422/61

[56] References Cited

U.S. PATENT DOCUMENTS

| | | | |
|---|---|---|---|
| 2,932,385 | 4/1960 | Bollmeier et al. | 206/219 |
| 3,770,199 | 11/1973 | Hoek et al. | 239/54 |
| 3,773,264 | 11/1973 | Cronan | 239/304 |
| 3,950,158 | 4/1976 | Gossett | 128/403 |
| 3,986,834 | 10/1976 | Steinbrink, Jr. | 422/61 |
| 4,106,478 | 8/1978 | Higashijima | 128/403 |

Primary Examiner—Andres Kashnikow
Assistant Examiner—Scott D. Malpede
Attorney, Agent, or Firm—Pennie & Edmonds

[57] ABSTRACT

A plastic packing device for the storage and the delivery of active materials consisting of multiple compartments destined to accommodate liquid, solid or gel materials, the compartments being formed by the joinder of two flexible polymeric sheets and comprising at least a sealed storage compartment impervious to the active materials and a sealed receiving compartment. At least one of the seams of the storage compartment is constituted by a system consisting of an internal layer of foam type plastic sheet which adheres on both its outer surfaces to leak-tight resilient polymeric sheets. External pressure on one of the compartments provokes internal rupture of the foam layer without rupture of outer polymeric sheets thus enabling emptying of storage compartment into receiving compartment without exposure of the active substance to the surrounding environment. The plastic packing is specially useful for ready premix of different components of useful active mixtures immediately before use. Utility is also apparent as easy-to-handle devices for the delivery of insecticides, malodor-counteractants or air-fresheners.

4 Claims, 6 Drawing Figures

MULTIPLE COMPARTMENT PLASTIC PACKING

CROSS-REFERENCE TO OTHER PENDING APPLICATIONS

This application is a continuation-in-part of application Ser. No. 432,917, filed Sept. 28, 1982.

FIELD OF THE INVENTION

The present invention is directed to improvements in the art of packaging, especially it relates to an improved package for ready to use (unit dose) active materials such as pharmaceuticals, insecticides, cosmetics, deodorizers or malodor-counteractants or air-fresheners.

This invention is especially valuable also for the packaging of inter-reactive materials, the use of which may be required in the admixed state immediately before use.

This invention has also particular utility for the manufacture of package devices destined to store for a prolonged period a volatile active substance, e.g. a perfume composition, before activation.

BACKGROUND OF THE INVENTION

Numerous pharmaceutical or chemically active substances are preferably used in the form of solutions or mixtures with other ingredients or excipients. However, in practice, many of these active substances ae less stable in solution than in their solid state, or even incompatible with certain of the other ingredients or additives present in the solution in question. This is due, in particular, to the fact that when these mixtures are heated, for example, during a sterilization process, or kept for long periods, they give rise to chemical reactions which render their constituents completely inactive or at least substantially decrease their activity.

In the case of a number of clinical infusion solutions, it has proved advantageous to use combinations of glucose and amino acids of various types. The drawback, which is at present difficult to overcome, of these combinations lies in the incompatibility of the products when they are heated, and in particular, in the case of sterilization. The aldehyde group of glucose in effect reacts with the free amino moiety of the amino acids such as lysine leading, via Maillard reaction, to the formation of Schiff bases which are the cause, inter alia, of the dark colouring of these solutions. This type of rection does not only lead to modification of the physical aspect of these solutions, but also has a detrimental effect on biological compatibility, thus making the solutions completely unsuitable for infusion.

One of the solutions proposed as a remedy for these drawbacks consists in replacing, in sterilizable mixtures for infusion, glucose by sorbitol, as this latter product does not have any free aldehyde group. However, sorbitol has several drawbacks which limit its use from the legal point of view.

On the other hand, articles of diverse types have been suggested for dispensing volatiles, eminently odoriferous materials, into the surrounding atmosphere. Pertinent prior art in this regard has been discussed for instance in U.S. Pat. No. 4,161,283. In particular, this document discloses an article for the slow release of volatilizable substances, the article being formed from opposed outer and inner wall members joined along their peripheral portions to define a central reservoir portion for receiving and confining a volatilizable substance. The outer wall member comprises a non-pourous flexible polymeric sheet material which does not permit bulk flow, but allows molecular diffusion therethrough. The inner wall member comprises an impermeable barrier layer. Another barrier layer is releasably bonded to the outer wall and prevents escape of the volatilizable substance until its removal at the time of desired use. An embodiment of the prior disclosed article comprises a strippable adhesive layer bounded to the outer surface of the inner wall impermeable layer and removal of the strippable layer enables adhesive bonding of the article to environmental surfaces.

Compartmented package devices have also been suggested in the past.

Representative prior art include in this respect, for examples, U.S. Pat. No. 3,343,664 which discloses a compartmented package for dispensing a fluid conditioning medium and comprising a sealed substantially air-free storage container filled with a fluid conditioning medium and adapted to be opened and emptied without exposure of the conditioner into a sealed air-free dispensing container having flexible and collapsible wall portions through which the conditioner is diffusible. The opening of the storage container is effected at the desired time of use by gripping two triangular ear portions, which terminate the lower part of the dispensing device, and pulling them in opposite directions. Because of differing elasticity (the walls of the dispensing container should be made substantially more elastic than those of the storage container), the walls of the dispensing container will stretch in response to the applied force while the wall of the storage container will tear through its lower seal at a point wherein a cut has been made, thereby opening the storage container U.S. Pat. No. 3,074,544 describes a multiple compartment flexible unitary package article for compartmentalized accomodation and selective admixture of at least two fluent materials which article comprises an envelope of flexible heat sealable sheet material, two opposing sidewalls of which are joined by heat sealing to form a transversely extending rupturable seam separating the interior of said envelope into individual compartments. In order to facilitate the rupture of the seam, this includes masking means in the form of a substantially uniformly open web interposed between said sidewalls and through the opening of which said sidewalls are heat sealed.

A device which has recently been developed for the perfuming of surrounding atmosphere comprises a pouch of specially adapted polymer material containing a perfuming solution (see International Patent Application WO 81/000051). These perform vapours diffuse slowly through the wall of polymer material and may thus perfume the environment for a long period. A problem arises, however, during the storage of these devices before activation.

In effect, as a result of the diffusion of the perfume vapours through the walls of polymer material of the packing, a considerable reduction in the initial amount of active substances may be observed.

To our knowledge, the above discussed prior art articles, though advantageous as they may seem, have not been commercialized so far. The reasons lie eminently in the difficulty encountered in their large scale manufacture especially in the realization of a reliable system enabling both safe storage of the active materials (or one of the active materials) and facility of activation by way of ready, "consumer-friendly" opening of the storage container.

It is an object of the present invention to provide a device which satisfies these apparently contradictory technical requirements.

THE INVENTION

The primay object of this invention is to provide a plastic packing for the storage and the delivery of active materials consisting of multiple compartments destined to accomodate liquid, solid or gel materials, said compartments being formed by the joinder of two flexible sheets of polymeric material, which packing is characterized in that it comprises:
- at least one sealed storage compartment impervious to the active materials, and
- a sealed receiving compartment, said storage compartment being limited at its periphery to form seams, at least one of which being constituted by a sheet of polymer material of the foam type which adheres on both its outer surfaces to leak-tight resilient polymeric sheets, said seam rupturing internally within the foam type material without rupture of the outer walls of the storage compartment when an external pressure is applied to one of the compartments so as to tear open said storage compartment and permit emptying of said active material into said receiving compartment without exposure of said material to the surrounding environment.

Another object of the instant invention is to provide a multiple compartment plastic packing of the above featured type in which the sealed receiving compartment is characterized by having at least one wall constituted by a polymeric sheet pervious to the useful active material so as to enable the diffusion of the vapours thereof into the surrounding environment.

Still another object of this invention is to provide a two compartment plastic packing of the above featured type wherein the storage compartment is housed within the receiving compartment and the opening of the said storage compartment is effected by applying an external pressure on the walls of the said receiving compartments.

A further object of this invention is to provide a plastic packing of the above featured type wherein the sheet of polymer material of the foam type is constituted by polyethylene, polypropylene, polyamide, polyvinyl chloride, polyester, polystyrene or any other material which is suitable and has a thickness of between about 0.005 and 0.2 mm approximately.

A still further object of this invention is to provide a sterilizable plastic packing made in accordance with the above featured type.

It is also an object of this invention to provide a multiple compartment plastic packing comprising a plurality of separate storage compartments, each containing an active material, which can be the same or different, adapted in such a way as to enable their opening and emptying into the receiving compartment thereby permitting selective mixing therein of said active materials.

PREFERRED EMBODIMENTS OF THE INVENTION

The plastic packing of the invention may, of course, be embodied in an aesthetically pleasing form. The receiving compartment can for instance be manufactured in order to acquire the form of a fruit or a flower. Its appearance can be made more functional and in this case, the packing may simply look like a pouch or an envelope. The walls can be made transparent so as to enable the consumer to control, for instance, the mixing of the active materials or, in the case of a room freshener, to observe the gradual consumption of the active fragrance composition.

The packing can moreover be housed in suitable container or simply hanged in the room it is desired to permeate.

The main and obvious advantage of the packing according to the invention is constituted by the possibility of ready activation immediately before use.

In comparison with systems having a weakened rupture zone, such as for example those having a partial indentation of the plastic sheets, a thinner tear zone, an adhesive joint or a heat-sealed tearing seam, this device having at least a seam formed by rupturable foam plastic material has the advantage that it only makes the breaking force dependent on the internal resistance of the sheet of foam and not on the quality of the seam or of the mechanically weakened zone. The internal resistance of the said sheet of foam does not depend solely on the type of polymer used for its manufacture but also, to a large extent, on the density of the said foam. Control of this latter factor therefore enables accurate monitoring of the rupture strength. This may in particular be maintained at a constant value during mass production of the packing devices. The thickness of the sheet of foam is preferably between 0.005 and 0.2 mm. This type of sheet may be commerically obtained (see in this respect the European Pat. No. 0004633). External walls, polymeric sheets, or cover sheets, can preferably be constituted by polyamide, polyester, polyethylene, polypropylene or ay other polymer material commonly used for the production of packing sheets.

These and other features of the present invention will become more apparent by taking the present description in conjunction with the accompanying drawings.

Figure 1:
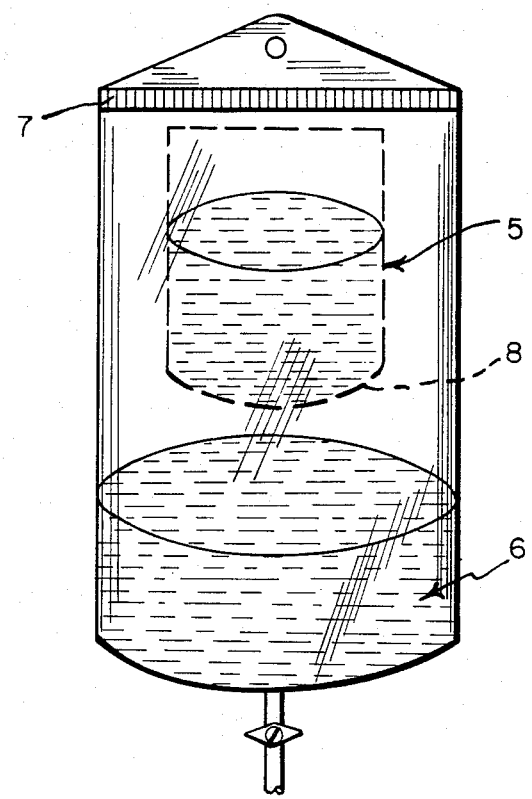
FIG. 1 is a view of a liquid filled packing obtained in accordance with a particular embodiment of the invention and specially designed for the packaging of active solutions for infusion. It comprises, in particular, a tearable internal poach (storage compartment) (5) and an outer casing (receiving compartment) (6) heat sealed together to form a solid joint (7). Rupturable seam (8) enables opening of the storage compartment upon exerting an external pressure on the flexible walls of the receiving compartment so as to enable emptying and mixing therein of the solution contained in the storage compartment with the solution contained in the receiving compartment. The upper ear section bears a hole in order to enable easy hanging.
Figure 2:
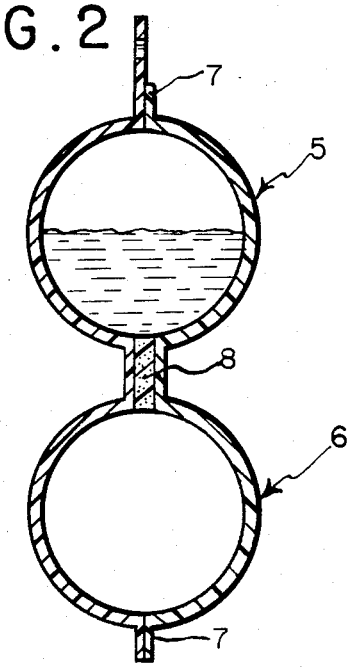
FIG. 2 is a cross-section through a packing having two compartments in accordance with an embodiment of the invention. In its upper and lower portions, it comprises a heat-sealed solid joint (7), whereas the two compartments are separated by a rupturable joint (8) in accordance with the invention.
Figure 3:
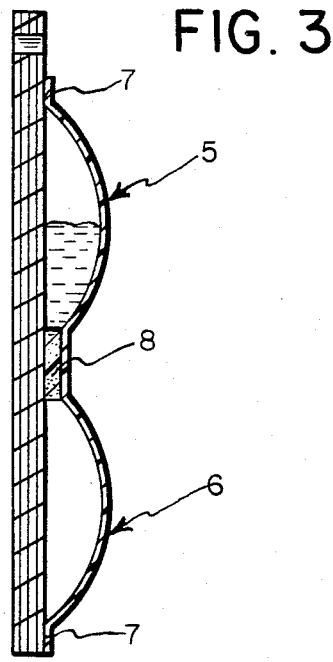
FIG. 3 is a longitudinal section through the same packing as in FIG. 2 and containing in its upper portion a liquid such as a perfume composition, the lower compartment being empty. The upper compartment is manufactured with plastic materials impervious to the active perfume composition, whereas the lower compartment is constituted by plastic material pervious to said active perfume composition. Diffusion of this perfume composition through the walls of the lower compartment followed by evaporation from the outer surface thereof into the surrouding environment (a room, a wardrobe or a car for example) provokes an air freshening effect. In its upper and lower portions, it comprises a solid heat-sealed joint (7), the two compartments being separated by a rupturable joint (8).
Figure 4:
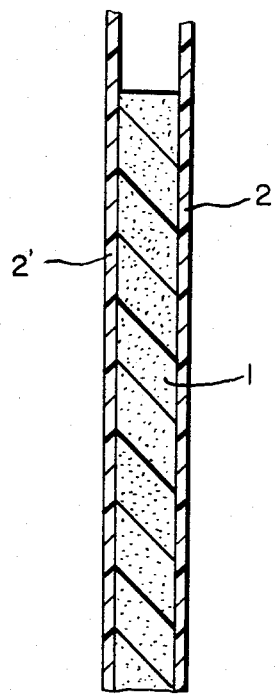
FIG. 4 is an enlarged section of a rupturable seam of the storage compartment constituted by a sheet of polymer material of the foam type (1) which adheres on both its outer surfaces to leak-tight resilient polymeric sheets (2) and (2').
Figure 5:
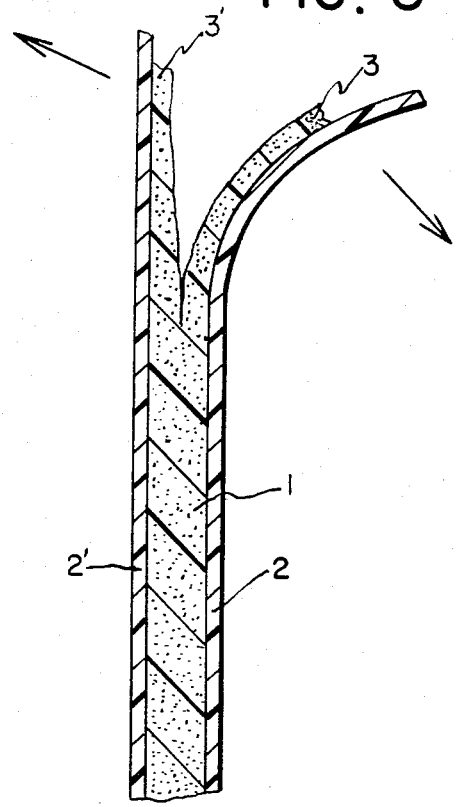
FIG. 5 is an enlarged section of this same joint when it is commencing its internal rupture upon applying a pressure on one of the compartments of the packing.
Figure 6:
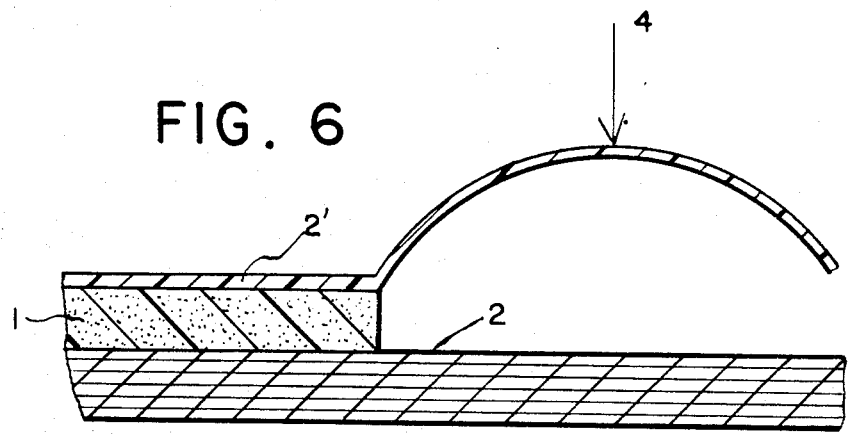
FIG. 6 is another enlarged section of the rupturble seam of the storage compartment together with a portion of the said compartment.

By exerting an external pressure (4) on its walls, a rupture occurs within the mass of the foam sheet constituting the rupturable seam. Rupture however does not occur between foam sheet and leak-tight outer sheets (2) and (2'), joined together by soldering or by means of an adhesive.

Foam sheets of the foam type has proved relatively resistant to transverse traction but may, in contrast, be readily broken into two portion [(3) and (3')] into a longitudinal plane. When a sheet (1) of this type is simply glued or heat sealed to two leak-tight sheets (2) and (2') they form an assembly of the "sandwich" type, it is then possible to separate this assembly by exerting a force, for instance, by means of applying a pressure on one of the flexible walls of a compartment. When separating, the foam sheet leaves two portions which both adhere to each of the tear-resistant leak-tight sheets.

What I claim is:

1. A plastic packing for the storage and the delivery of active materials containing multiple compartments to accomodate liquid, solid or gel materials, said compartments being formed by the joinder of two flexible sheets of polymeric plastic materials, which packing is characterized in that it comprises:
   at least one sealed storage compartment impervious to the active materials, and
   a sealed receiving compartment, said storage compartment being limited at its periphery by seams, at least one of which being constituted by a sheet of rupturable polymer plastic foam material which adheres on both its outer surfaces to leak-tight resilient polymeric plastic sheets, said seam rupturing internally within the foam material without rupture of the outer walls of the storage compartment when an external pressure is applied to one of the compartments to tear open said storage compartment and permit emptying of said active material into said receiving compartment without exposure of said material to the surrounding environment.

2. A plastic packing according to claim 1, wherein the sealed receiving compartment is characterized by having at least one wall constituted by a polymeric sheet pervious to the useful active material so as to enable the diffusion of the vapours thereof into the surrounding environment.

3. A two compartment plastic packing in accordance with claim 1, wherein the storage compartment is housed within the receiving compartment and the opening of the said storage compartment is effected by applying an external pressure on the walls of the said receiving compartment.

4. A plastic packing in accordance with claim 1, wherein the sheet of polymer plastic foam material is selected from polyethylene, polypropylene, polyamide, polyvinyl chloride, polyester, or polystyrene foam and has a thickness of between about 0.005 and 0.2 mm.

* * * * *